United States Patent [19]

Dearling

[11] 4,165,835

[45] Aug. 28, 1979

[54] COMBINED FRAGRANCE DISPENSER AND HUMIDIFIER

[76] Inventor: Harry S. Dearling, 25 E. 83rd St., New York, N.Y. 10028

[21] Appl. No.: 862,771

[22] Filed: Dec. 21, 1977

[51] Int. Cl.² .............................................. A61L 9/04
[52] U.S. Cl. ..................................... 239/51.5; 239/45
[58] Field of Search ................... 239/44, 45, 47, 51.5, 239/57–60; 21/108, 121–126

[56] References Cited

U.S. PATENT DOCUMENTS

| 1,984,055 | 12/1934 | Carter | 239/51.5 |
| 2,383,960 | 9/1945 | Duduy | 239/51.5 |
| 3,400,890 | 9/1968 | Gould | 239/60 X |

Primary Examiner—Robert W. Saifer
Attorney, Agent, or Firm—Curtis, Morris & Safford

[57] ABSTRACT

A combined fragrance dispenser and humidifier includes a vessel to hold a quantity of water, an absorbent carrier member having one end in contact with the water and another end in air circulating relationship with a fragrance retaining member so that air circulates through the absorbent carrier member allowing the water vapor to evaporate while passing over the fragrance to dissipate the fragrance as well.

5 Claims, 8 Drawing Figures

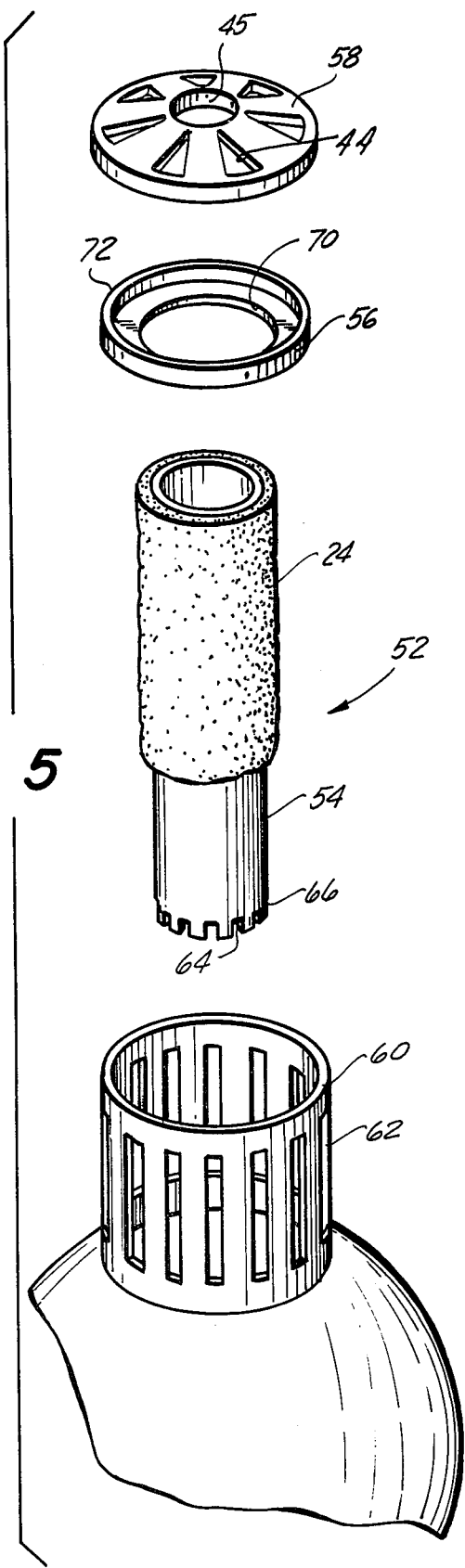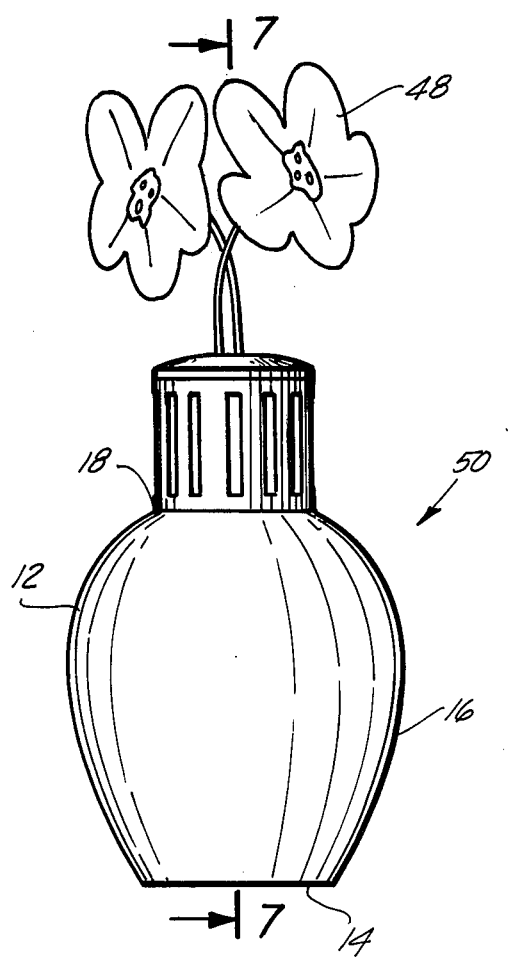

COMBINED FRAGRANCE DISPENSER AND HUMIDIFIER

The present invention relates to a room humidifier and fragrance dispenser and more particularly to such room humidifiers and fragrance dispensers which combine the function of room humidification and fragrance dissipation.

Broadly, the present invention comprises a chamber or vessel adapted to hold a quantity of a liquid such as water, an absorbent carrier member disposed within the vessel and having one end in contact with the water and another end disposed above the liquid level, a fragrance retaining member, which may be either another absorbent member or a cup or dish to retain a quantity of a fragrant liquor disposed in contact with the absorbent carrier member. The absorbent carrier member and fragrance retaining member are disposed within a housing permitting air flow through and around the carrier member and the fragrance retaining member so as to permit the evaporation of water vapor with a concomitant entrapment or entraining of a fragrant scent.

The combined humidifier and fragrance dispenser of the present invention is especially adapted for use as a home or room humidifier and fragrance dispenser and provides the dual advantageous purpose of humidifying the air within the room by the slow controlled dissipation of water vapor into the air as well as providing a continuous means to pleasantly scent the air in a room by slow and protracted dissipation of the desired fragrance.

Accordingly, it is an object of the present invention to provide a combined humidifier and scent dispensing device which is pleasant in appearance and relatively inexpensive to manufacture.

It is a further object of the present invention to provide such a combined humidifier and fragrance dispenser which permits humidification of a room through the dissipation of water vapor into the room as well as permitting pleasant scenting of the room by dissipation of a fragrance with the evaporation of water vapor.

These and other objects and advantages of the present invention will become more readily apparent after consideration of the following specification and accompanying drawing wherein:

FIG. 5 is an exploded perspective view of the housing of an alternate embodiment of the present invention;

FIG. 6 is an elevational plan view of the embodiment shown in FIG. 5;

Figure 1:
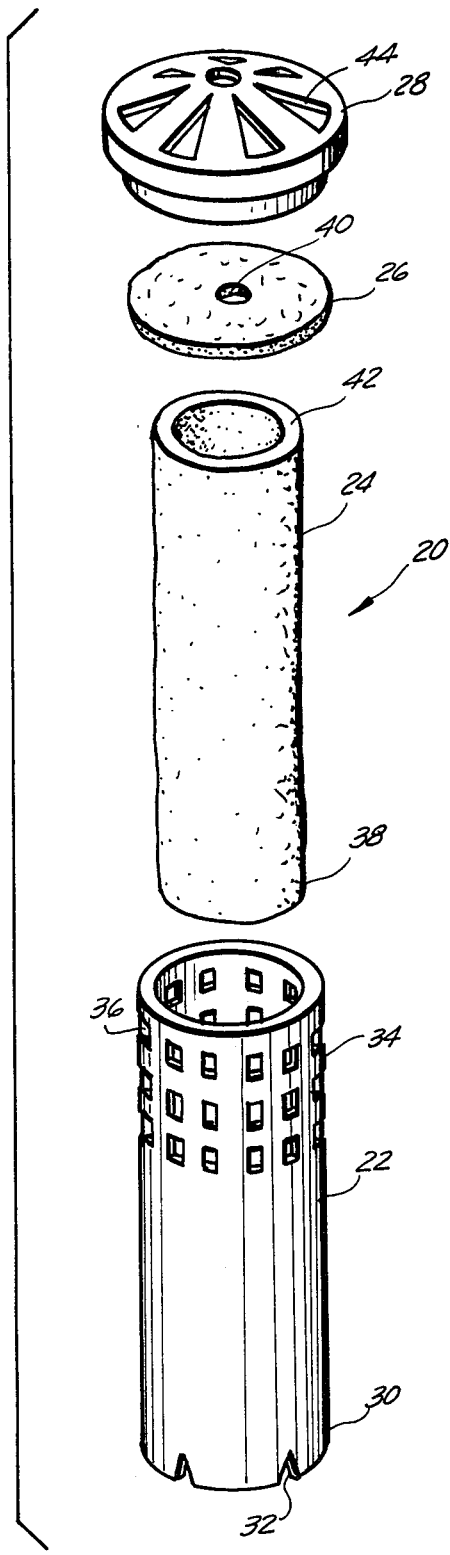
FIG. 1 is an exploded perspective view of one embodiment of the housing for the combined humidifier and fragrance dispenser of the present invention.
Figure 2:
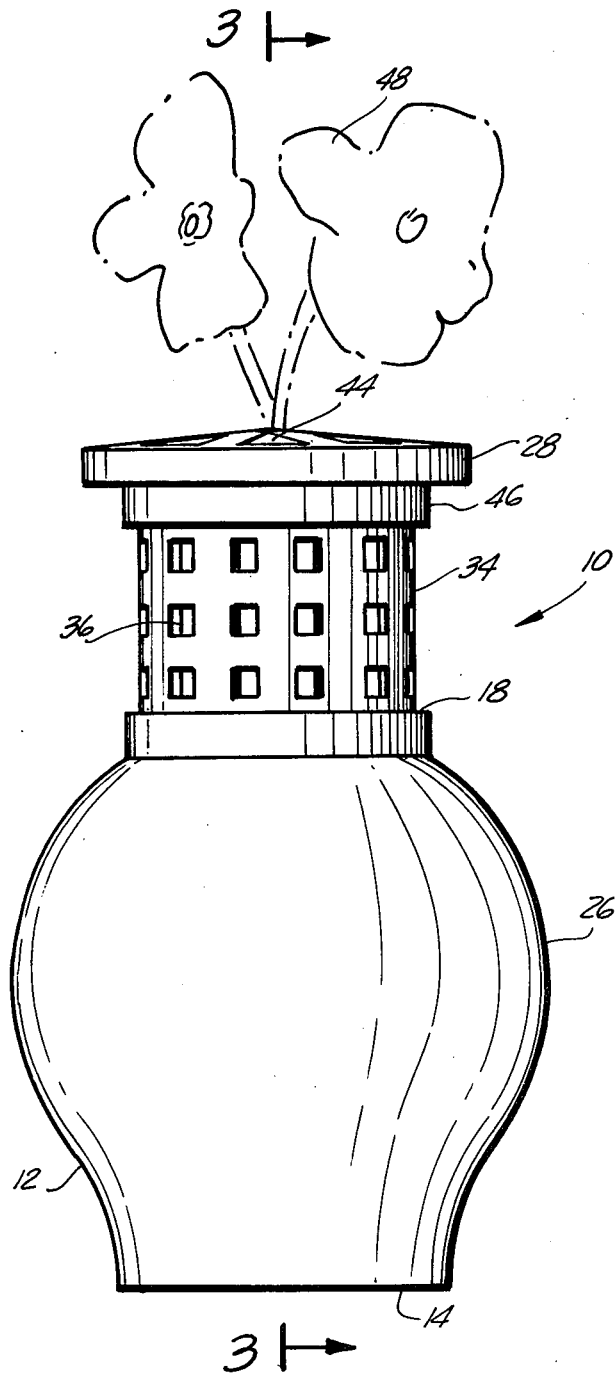
FIG. 2 is an elevational view of the embodiment of the combined humidifier and fragrance dispenser shown in FIG. 1.
Figure 3:
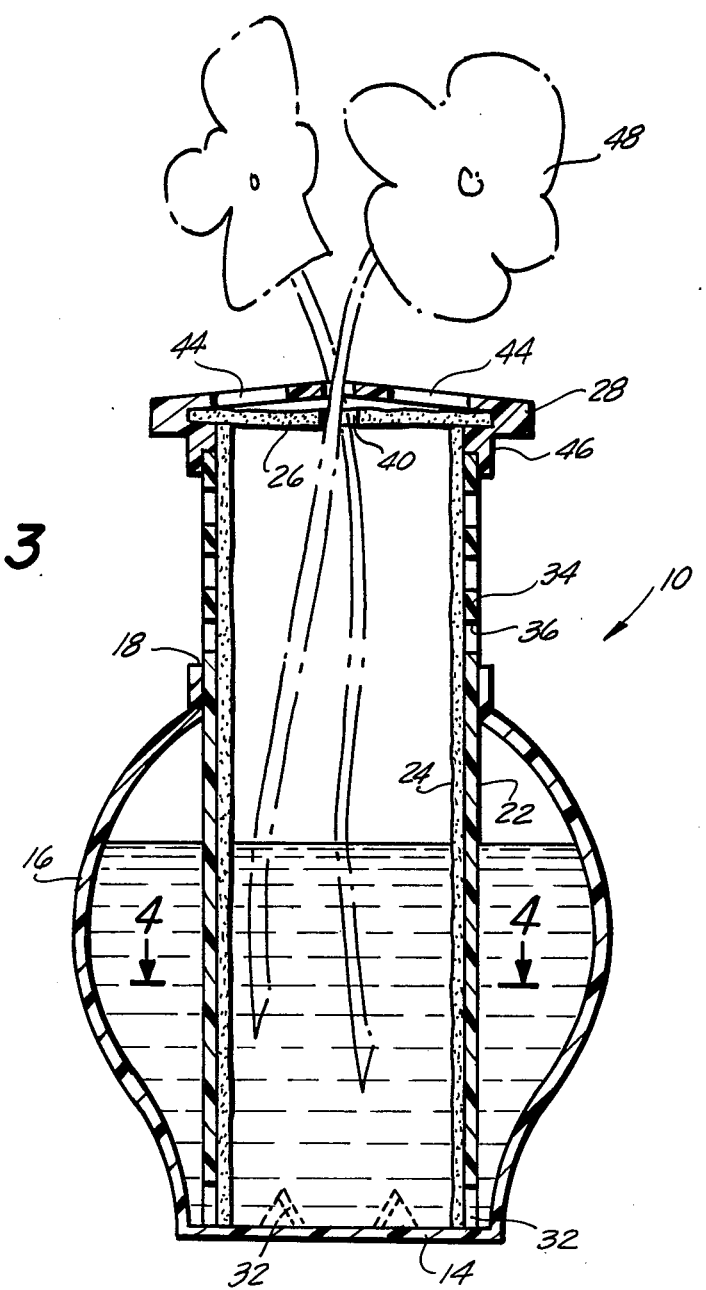
FIG. 3 is a sectional view taken along line 3—3 of FIG. 2.
Figure 4:
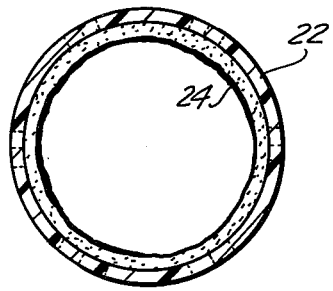
FIG. 4 is a cross-sectional view taken along line 4—4 of FIG. 3.
Figure 7:
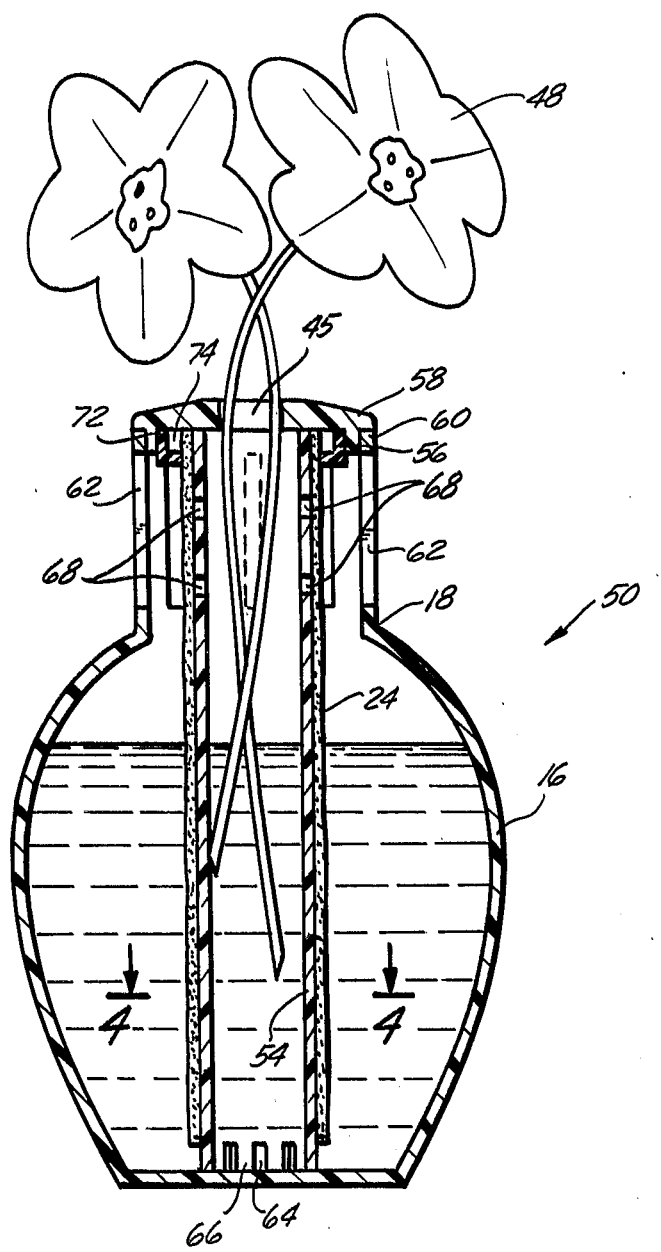
FIG. 7 is a vertical section taken along line 7—7 of FIG. 6.
Figure 8:
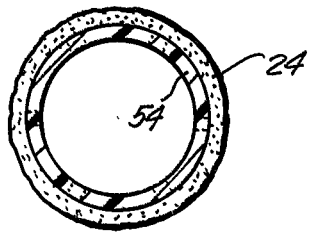
FIG. 8 is a horizontal sectional view taken along line 8—8 of FIG. 7.

With reference to the drawings, and particularly FIGS. 1 and 4, there is shown a combined fragrance dispenser and humidifier 10 which includes a vessel or container 12, preferably formed in an aesthetic and appealing shape, to hold a quantity of a liquid such as water. As illustrated in FIG. 2, container 12 includes a base 14, an intermediate body portion 26 and an open top segment 18.

Disposed within the container 12 is a housing assembly 20, shown in exploded perspective view in FIG. 1, which includes a sleeve member 22 within which is disposed a carrier member 24 of an absorbent and air permeable material, a fragrance retaining member 26 and a cap member 28.

Sleeve 22 is cylindrical in shape and includes a lower segment 30 within which is formed a plurality of notches 32 spaced about the circumferential extent of the sleeve 22. The upper segment 34 of sleeve 22 includes a plurality of openings 36 which may be arranged in any aesthetically appealing pattern. The length of sleeve 22 is such as to extend above the open end 18 of the container 12 with the sleeve positioned in the container and segment 34 of sleeve 22 being dimensioned so that the plurality of openings 36 are above the open top 18 of vessel 12.

The carrier member 24 is also cylindrical in shape and is dimensioned to telescopically fit within sleeve 22. Because of the absorbent nature of carrier member 24, when sleeve 22 with the carrier member 24 is inserted into container 12 and liquid is added to container 12, the liquid contacts lower portion 38 of the carrier member 24. As the liquid flows into contact with this section of the carrier member through the notches 32 formed in the lower end of sleeve 22, liquid is absorbed into the carrier member and flows by capillary action up the carrier member 24 to completely wet the carrier member. Because the access openings 36 expose that portion of the carrier member extending above open top 18 of container 12 to the air, air flow is generated through the access openings 36 to the carrier member 24 and through the carrier member 24 to cause evaporation of the water absorbed by the carrier member thereby providing a humidifying action to any room in which the container 12 is disposed.

The fragrance retaining member 26 is selected from a material, such as sponge material or felt-like material, which absorbs and retains a fragrantly scented liquor and retains the scent for an extended period of time. Carrier 26 is formed as a circular wafer having an access opening 40 therein and is disposed on the upper end 42 of the carrier member 24 so that the capillary wetting imparted to carrier member 24 is also imparted to the fragrance retaining member 26 to wet member 26 as well. In this manner, with fragrance retaining member 26 in contact with carrier member 24 water is absorbed by fragrance retaining member 26 to activate the fragrance retained by that member to allow dissipation of that fragrance as water vapor is evaporated from fragrance retaining member 26.

A decorative end cover 28 is also provided which includes suitable openings 44 and a central aperture 45 therein on its upper surface to provide air flow access from the interior of carrier member 24 through the access opening 40 as well as through the somewhat permeable fragrance retaining wafer 26. End cap 28 also includes a lower depending segment 46 dimensioned to telescopingly fit over the upper end of sleeve 22 providing a pleasing and aesthetic as well as functional cover for the device. Suitable decorative flowers, shown at 48, may also be provided in order to enhance the physical appearance of the combined humidifier and fragrant dispenser when the device is placed within a room.

With reference now to FIGS. 5 through 8, an alternate embodiment 50 of the combined fragrance dispenser and humidifier is shown. In the description of this embodiment like reference numerals will be used to designate elements similar to the elements shown in the embodiment of FIGS. 1 through 4. Thus, as illustrated in FIG. 6, the combined fragrance dispenser and humidifier 50 includes a vessel or container 12 having a base 14, intermediate body portion 16 and an open top segment 18. Disposed within the container 12 is a housing assembly 52, shown in exploded perspective view in FIG. 5, which includes a sleeve member 54 about which is disposed the carrier member 24, a fragrance retaining member 56 and a cap member 58. A sleeve extension member 60 is also provided having a cylindrical shape and a plurality of longitudinal through slots 62 to permit air flow therethrough. The sleeve extension member 60 is adapted to be positioned about the open top segment 18 of container 12.

Sleeve 54 includes a plurality of notches 64 cut in its lower end 66 to provide a support for the sleeve on the base 14 of container 12. Sleeve 54 also includes a plurality of apertures 68 in its upper end to permit air flow through the moistened carrier member 24 into the interior of sleeve 54.

The fragrance retaining member 56 is a disc-like member having a circular opening 70 therein adapted to fit about carrier member 24 and sleeve 54 and includes a peripheral lip or rim 72 which in conjunction with the upper end of carrier member 24 defines an annular channel 74 (see FIG. 7) in which may be disposed a liquid or gelatin type fragrant liquor adapted to slowly evaporate and dissipate its fragrance as it evaporates.

As in the embodiment of FIGS. 1 through 4 the cap member 58 includes a plurality of openings 44 therein as well as a central aperture 45 to permit air flow from the interior of sleeve 54 and from the annular channel 74 for dissipation of the fragrance and the evaporated water vapor.

The combined fragrance dispenser and humidifier of the present invention provides a readily usable and aesthetically pleasing device which conveniently allows for dissipation of a pleasing aroma or scent while also providing the desirable function of air humidification. By its construction an air flow is set up around and through the fragrance dispenser to cause evaporation of water absorbed on the carrier member with the air flow pattern designed to flow about a fragrance source to entrain the fragrance in the evaporated water vapor and air. In this manner a steady and controlled humidification is provided as well as dissipation of a selected fragrance.

What is claimed is:

1. A fragrance dispenser and humidifier comprising a vessel for holding a quantity of an evaporable liquid, means within said vessel for absorbing a quantity of said liquid to a height disposed above the surface of said liquid in said vessel, means disposed about said absorbing means to direct an air flow pattern about said absorbing means to initiate evaporation of said absorbed liquid and means operatively associated with said means disposed about said absorbing means to dissipate a selected fragrance within the air and evaporated liquid thereby to dissipate a fragrance within liquid evaporated from said vessel.

2. A fragrance dispenser and humidifier as defined in claim 1 wherein said absorbing means includes a carrier member of an absorbent and air permeable material formed in a cylindrical shape and disposed to have one end within said liquid and its other end above the surface of said liquid and said means disposed about said absorbing means includes a sleeve member telescoped about said carrier member.

3. A fragrance dispenser and humidifier as defined in claim 2 wherein said carrier member and sleeve member extend above the upper portion of said vessel and wherein said sleeve member includes openings therethrough spaced about its periphery above the upper portion of said vessel to provide an air flow path from exterior said sleeve member to the interim.

4. A fragrance dispenser and humidifier as defined in claim 3 wherein said means to dissipate a selected fragrance includes a fragrance containing member impregnated with a selected fragrance disposed in contact with said carrier member thereby to become wet by capillary action adapted to dissipate a fragrance as liquid is evaporated from said fragrance retaining member.

5. A fragrance dispenser and humidifier as defined in claim 3 wherein said means to dissipate a selected fragrance includes a fragrance retaining member disposed about said carrier member adapted to hold a quantity of an evaporable fragrance liquor, said fragrance liquor being evaporable into vapor evaporating from said carrier member.

* * * * *